United States Patent [19]

Kawaguchi et al.

[11] Patent Number: 5,122,600
[45] Date of Patent: Jun. 16, 1992

[54] DNA-IMMOBILIZED MICROSPHERES AND A PROCESS FOR PURIFYING A DNA-TRANSCRIPTION-CONTROLLING FACTOR USING THE SAME

[75] Inventors: Haruma Kawaguchi, Yokohama; Akira Asai, Fujisawa; Yasuji Ohtsuka; Hiroshi Handa, both of Tokyo, all of Japan

[73] Assignee: Nippon Zeon Co., Ltd., Tokyo, Japan

[21] Appl. No.: 411,127

[22] Filed: Sep. 22, 1989

[30] Foreign Application Priority Data

Sep. 24, 1988 [JP] Japan .................. 63-239239

[51] Int. Cl.$^5$ ............................. C07H 17/00
[52] U.S. Cl. ........................ 536/27; 435/6; 435/91
[58] Field of Search ............... 536/27; 435/6, 91

[56] References Cited

U.S. PATENT DOCUMENTS 4,806,546 4/1989 Carrico et al. ............... 536/27
4,806,631 4/1989 Carrico et al. ............... 536/27
4,912,032 3/1990 Hoffman et al. ............... 435/7

OTHER PUBLICATIONS

Chem. Abstract 111:150064y, 1989.

Primary Examiner—John W. Rollins
Attorney, Agent, or Firm—Armstrong, Nikaido, Marmelstein, Kubovcik & Murray

[57] ABSTRACT

There are disclosed a DNA-immobilized microsphere comprising DNA chains having base sequences which bind a specific protein specifically, and a carrier having a particle size of not more than 50 μm and not less than 0.01 μm which does not adsorb any protein, said carrier and said DNA chains being bound to each other by a chemical bond, and a process for purifying a protein using said microsphere.

10 Claims, 4 Drawing Sheets

1  2  3  4

DNA-IMMOBILIZED MICROSPHERES AND A PROCESS FOR PURIFYING A DNA-TRANSCRIPTION-CONTROLLING FACTOR USING THE SAME

BACKGROUND OF THE INVENTION

1. Field of the Invention

The present invention relates to DNA-immobilized microspheres used, for example, for purifying a protein. More particularly, it relates to DNA-immobilized microspheres comprising DNA chains having base sequences capable specifically of binding a transcription-controlling factor protein, and a carrier which does not adsorb any protein, the DNA chains and the carrier being chemically bound to each other. Said DNA-immobilized microspheres are used in a process for purifying a transcription-controlling factor which comprises adsorbing the transcription-controlling factor on the DNA chains having base sequences capable specifically of binding the transcription-controlling factor protein, removing other proteins, and then releasing the transcription-controlling factor from the DNA chains.

2. Related Art

One of the main branches of genetic engineering which has been greatly advanced in recent years is analysis of genes themselves. In an analysis, analysis of transcription-controlling factors leads to elucidation of the mechanism of transcriptional control in genes and hence is important.

Transcription is a process of synthesis of RNA in accordance with DNA as gene by RNA polymerase and is divided into initiation, elongation and termination steps.

In the transcription initiation step, RNA polymerase binds to a specific base sequence of DNA which is called "promoter", to initiate transcription. It is considered that in the promoter of procaryotic cells, a base sequence called "Pribnow box" which is located about 10 base pairs upstream to the transcription initiation site (this base sequence is basically TATAAT though somewhat different depending on promoter), is a site to which RNA polymerase actually binds. A certain protein binds to a specific base sequence called "operator" to accelerate or suppress the transcription from the promoter. In the case of eucaryotic cells, it is suggested that a base sequence called "TATA box" or "Goldberg-Hogness box" which is located 20 to 30 base pairs upstream to the transcription initiation site [this base sequence is basically TATA$_T^4$A$_T^4$ ($_T^4$ represents A or T) though somewhat different depending on promoter], determines the initiation of transcription. A factor is separated and binds to the TATA box to control the transcription. As to the control of the amount of the transcription, it is considered that there exists a characteristic, a specific base sequence upstream to TATA box, which participates in the transcriptional control of each gene. In addition, there is a specific base sequence called "enhancer" which enhances the transcriptional efficiency. Three kinds of RNA polymerases are present in eucaryotic cells: RNA polymerase II participates in the usual synthesis of a mRNA precursor, RNA polymerase I in synthesis of ribosomal RNA, and RNA polymerase III in synthesis of 5S RNA and tRNA. For each of these syntheses, there exist regulatory genes specific for the transcription for the synthesis.

In the transcription elongation step, in the case of procaryotic cells, a sequence called "attenuator" exists as a transcription termination signal inside an operon and controls the gene expression. In the case of animal cells, substantially no regulatory signal corresponding to an attenuator have been reported, but it has been suggested that such a regulatory signal is present in the late gene region of Simian Virus 40.

In the transcription termination step, in the case of procaryotic cells, there exist base sequences called "terminators" which order termination of transcription. The terminators of *Escherichia coli* are roughly divided into those requiring a protein factor called "$\rho$ factor" ($\rho$-dependent terminators) and those requiring no $\rho$ factor ($\rho$-independent terminators). The terminators are complicatedly controlled by participation of λN antitermination protein or the like. In the case of eucaryotic cells, the transcription termination step has been investigated but has not yet been elucidated.

Thus, a large number of signals in a gene participate in transcription. Many of the signals function by interaction with transcription-controlling factors which are proteins. Elucidation and utilization of the mechanism of such transcription will lead to great progress, for example, in control of biogenic actions and production of useful materials by genetic engineering, and are of important significance in the fields of medicines, fermentation, etc.

For analysis of the important transcription-controlling factors in a gene, it is necessary to separate and purify a protein which acts as the controlling factor. But, such a transcription-controlling factor protein only exist in very small amounts and hence is difficult to purify. A transcription-controlling factor protein which binds directly to a gene is separated and purified by affinity chromatography using DNA chains containing binding sites, as a ligand, and gel particles of cellulose, agarose, etc. have been used therefor. However, most of these gels on the market have a particle size of more than several tens of micrometers, a small total area of particle surface, and a wide particle size distribution, and hence cannot be said to be sufficient in efficiency, reproducibility, etc. when used for the purpose described above. Furthermore, when the gel particles are packed in a column, a solution cannot be passed through the column at a high pressure from the viewpoint of the strength of the gel particles because the gel particles contain water at more than several tens of times as much as the gel particles. Therefore they are not efficient.

SUMMARY OF THE INVENTION

The present inventors earnestly investigated and consequently found that a protein as transcription-controlling factor can be obtained easily in high yield by using carriers obtained by chemically attaching a synthetic DNA chains having base sequences to which the protein as a transcription-controlling factor binds specifically, to synthetic polymer particles having no nonspecific adsorbability, whereby the present invention has been accomplished.

The first aspect of this invention is to provide DNA-immobilized microspheres comprising DNA chains having base sequences capable of binding a specific protein and a carrier which does not adsorb any protein, the carrier and the DNA chains being chemically bound to each other. The second aspect of this invention is to provide a process for purifying a specific protein which comprises adsorbing the specific protein on DNA-immobilized microspheres, one microsphere comprising DNA chains having base sequences capable of specifically binding the specific protein and a carrier which does not adsorb any protein (the carrier and the DNA chains being chemically bound to each other), through the DNA chains, removing other proteins, and then releasing the specific protein from the DNA chains.

DESCRIPTION OF THE PREFERRED EMBODIMENTS

Figure 1:
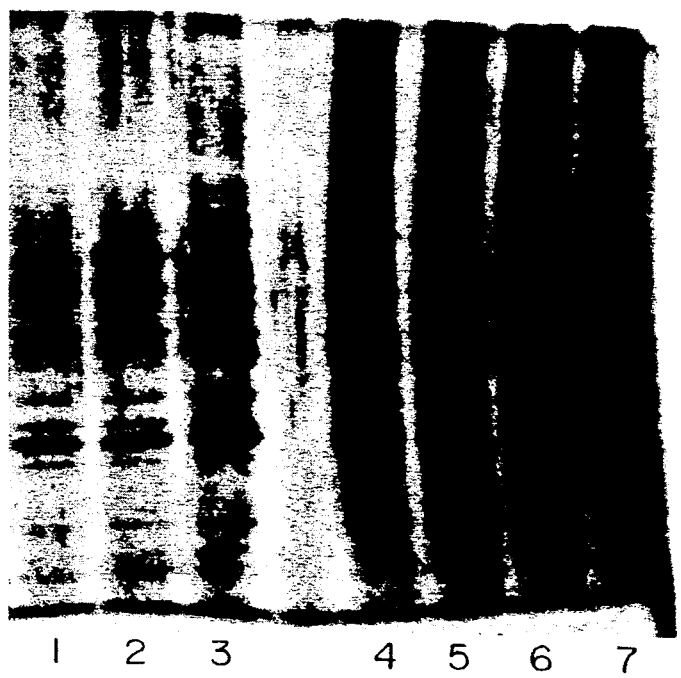
FIG. 1 shows an electrophoretic pattern of a supernatant of a mixture of glycidyl methacrylate polymer particles which have been made hydrophilic and unpurified protein solution, and a supernatant of a mixture of styrene-glycidyl methacrylate copolymer particles which have been made hydrophilic and unpurified protein solution.

The carrier which does not adsorb any protein, in this invention is such that protein is not non-specifically adsorbed on the surface of carrier particles by physical adsorption or the like. In general, various proteins tend to be adsorbed on a hydrophobic particle surface. Therefore, in the present invention, it is essential that the particle surface should not be hydrophobic. As monomers for hydrophilic polymeric compounds, there can be exemplified, for example, ethylene-oxide-containing (meth)acrylic acid esters such as ethylene glycol (meth)acrylate, triethylene glycol (meth)acrylate, etc., hydroxy-group-containing (meth)acrylic acid esters such as hydroxymethyl (meth)acrylate, hydroxypropyl (meth)acrylate, etc., epoxy-group-containing (meth)acrylic acid esters such as glycidyl (meth)acrylate, etc., (meth)acrylic acid alkyl esters such as methyl (meth)acrylate, ethyl (meth)acrylate, etc., monoethylenic unsaturated amide monomers such as acrylamide, methacrylamide, diacetoacrylamide, N-hydroxymethylacrylamide, etc., and ethylenic unsaturated nitrile compounds such as acrylonitrile, methacrylonitrile, etc. Either homopolymers or copolymers of these monomers can be used as the carrier particles of this invention. Homopolymers or copolymers of non-hydrophilic monomers can also be used without any limitation so long as they do not cause non-specific adsorption of proteins on the particle surface. In the present invention, glycidyl methacrylate polymers (hereinafter referred to as "poly-CMA") is particularly preferable from the viewpoint of prevention of non-specific adsorption of proteins.

A method for producing the particles of this invention is not critical so long as it does not result in nonspecific adsorption of proteins on the particle surface, and suspension polymerization and emulsion polymerization can be employed for the production. When suspension polymerization is employed, assistant materials for polymerization are not critical so long as they do not cause non-specific adsorption of proteins on the particle surfacer. As dispersion stabilizers, there can be exemplified water-soluble polymers such as polyacrylamides, limited-hydrolysis products thereof, polyacrylic acids, hydroxypropylcelluloses, ethyl celluloses, methyl celluloses, polyvinyl alcohols, polyvinyl acetates, etc. As polymerization initiators, there can be used, for example, azo initiators such as azobisisobutylonitrile, etc., and peroxides such as benzoyl peroxide, etc. Also when emulsion polymerization is employed, assistant materials for polymerization are not critical so long as they are used for usual emulsion polymerization and do not cause non-specific adsorption of proteins on the particle surface. There can be used, for example, surfactants such as anionic surfactants (e.g. sodium dodecylbenzene-sulfonate, etc.) and non-ionic surfactants (e.g. polyoxyethylene nonyl phenyl ether, etc.), builders such as sodium sulfate and the like, inorganic dispersion stabilizers such as hexametaphosphoric acid and the like, and polymerization initiators such as potassium persulfate and the like. A method for the emulsion polymerization is also not critical and there can be used conventional polymerization methods such as batch method, semi-batch method, continuous method, etc.

As the emulsion polymerization employed in this invention, it is particularly preferable to employ soapfree emulsion polymerization using only water, monomer(s) and polymerization initiator, for forming a clean particle surface and preventing non-specific adsorption of proteins.

The particles may be either those composed of homopolymer or copolymer, or those having a core-shell structure, so long as they do not cause non-specific adsorption of proteins. However, in the case of particles having a core-shell structure, when the core is made of a material on which proteins are non-specifically adsorbed, its surface should be completely coated and moreover the core should have sufficient strength for preventing the surface from peeling or the like during purification.

The carrier of this invention, unlike gel particles, permits easy control of its quality because its particle size distribution can be narrowed, for example, by controlling the polymerization reaction.

As the carrier, one which binds DNA chains in a large amount per unit volume is preferable for the purpose of use, i.e., purification. For this reason, the smaller the particle size, the more preferable the carrier. This is because when the particle size is small, the surface area per unit volume is increased, so that sites to which DNA chains can bind are increased. A carrier having a particle size of 50 $\mu$m or less, preferably 20 $\mu$m or less is effective.

Any carrier can be used for purifying a protein so long as it has a particle size of 0.01 $\mu$m or more, preferably 0.2 $\mu$m or more and can be utilized for separation and purification by a batch process in which the protein is adsorbed on DNA chains and then separated from a sample. For example, poly-GMA has a sufficient specific gravity, permits precipitation of the carrier by centrifugation and its separation from the supernatant, and can be used for purifying a protein by a batch process.

However, when the carrier is used for affinity chromatography, the particle size is preferably 3 $\mu$m or more for packing and retention in a column. This is because there is no material which satisfies conditions required of a material for preventing outflow of the carrier from a column and can prevent outflow of particles having a particle size of less than 3 $\mu$m.

Although immobilization of DNA chains on the surface of the particles thus obtained is carried out by a covalent bonding method, a method for the immobilization is not critical so long as it does not cause nonspecific adsorption of proteins on the particle surface and the immobilization can be carried out by a conventional method. In general, a DNA chain can be immobilized on the particle surface, for example, by a carbodiimide method using carboxylic acid groups in the particle surface, a cyanogen bromide method using hydroxyl groups in the particle surface, a glutaraldehyde or diazo method using amino groups in the surface, or an epoxide method using epoxy groups in the surface.

With an increase of the amount of DNA chains binding to the carrier, the amount of a specific protein bound to the carrier through the DNA chain is increased. Thus, a large amount of DNA chains binding to the carrier is desirable for the purpose of use, i.e., purification and hence it is recommendable to choose conditions under which a large amount can be attained.

The DNA chain used in this invention is a double-stranded one. When it is a single-stranded one, there is a fear that the middle of the DNA chain takes part in its immobilization on the particles. Furthermore, non-specific adsorption of proteins tends to occur. The DNA chain has base sequences which can bind to a specific protein specifically. An objective protein is selected from proteins which bind to the DNA chain, and a specific base sequence is chosen depending on the objective protein. For improving the efficiency of purification, a DNA chain containing in the molecule a plurality of specific base sequences which bind to a specific protein is preferable. The protein which binds to specific bases specifically includes, for example, transcription-controlling factor proteins.

Purification of a protein using the DNA-immobilized microspheres is carried out by adsorbing the objective protein on the DNA-immobilized microspheres, removing other proteins, and then releasing the specific protein from the DNA chains. The adsorption of the objective protein is carried out by bringing the DNA-immobilized microspheres into contact with a liquid containing the objective protein, for example, cell extract. A method for the contact is not critical so long as there are employed conditions under which the objective protein has an activity to bind to the specific base sequence. A method for the removal of other proteins is also not critical. For example, it is sufficient that the DNA-immobilized microspheres are sufficiently washed with a buffer solution which contains no protein and does not inactivate proteins, under conditions under which the bound protein is not released. A method for the release of the objective protein is also not critical. For example when the DNA-immobilized microspheres are placed in a buffer solution having a high salt concentration, the objective protein is released. These methods can be practiced either by an affinity chromatography using a column, or by a batch process.

The objective protein is inactivated in some cases by the above-mentioned procedures of adsorption, washing and release, depending on these procedures. For purifying the objective protein without inactivation, these procedures should be carried out under conditions under which the objective protein is not inactivated.

The particles of this invention are harder than gels and contain no water, and therefore when packed in a column, they permit passage of a solution through the column at a high pressure and hence efficient purification. A conventional column chromatography using a gel requires a large amount of buffer solutions, so that a purified protein is diluted. On the other hand, in purification using the particles of this invention, the degree of dilution of the objective protein in the case of column chromatography is, of course, low. Moreover, also in the case of a batch process, a purified protein can be obtained easily without dilution, by precipitation of the particles, etc. These facts are very advantageous for purification of trace proteins such as transcription-controlling factor proteins.

As described in the examples given hereinafter, a transcription-controlling factor E4TF1 was purified for the first time by a purification process using the DNA-immobilized microspheres of this invention, which were thus proved to be excellent for a purification process.

Thus, according to the present invention, a specific protein which binds to a specific base sequence, in particular, a transcription-controlling factor protein can be efficiently separated and purified.

EXAMPLES

The present invention is more concretely explained with reference to the following examples.

EXAMPLE 1

To 160 ml of water were added 10 g of monomer GMA and 0.2 g of potassium persulfate as polymerization initiator, and soap-free emulsion polymerization of GMA was carried out at 70° C. for 24 hours with stirring by means of a stirrer at a rate of 200 r.p.m. The resulting poly-GMA particles were precipitated by centrifugation, and after removal of the supernatant, the particles were dispersed in distilled water. This washing procedure was repeated 3 times. The poly-GMA thus obtained had an average particle size of 0.23 $\mu$m.

As a comparative example, styrene-glycidyl methacrylate copolymer particles (hereinafter referred to as "St-GMA particles") having an average particle size of 0.50 $\mu$m were obtained by adding 14 g of monomer styrene, 6 g of monomer GMA and 0.2 g of potassium persulfate to 160 ml of water, and carrying out soap-free emulsion polymerization under the same conditions as for the polymerization of GMA.

An extract from the nucleus of HeLa cells was charged into a column of heparin Sepharose, eluted with 0.1 M KCl, charged into a column of DEAE Sepharose, and then eluted with 0.35 M KCl to prepare a protein solution (solvent: 0.1 M KCl Tris buffer, pH 7.9).

With 200 $\mu$l of the above unpurified protein solution were mixed 200 $\mu$g of the poly-GMA particles or the St-GMA particles, both of which had been made hydrophilic by acid treatment. Thereafter, each of the mixtures thus obtained was centrifuged to precipitate the particles, and the supernatant was collected and then subjected to polyacrylamide electrophoresis.

The electrophoretic pattern obtained is shown in FIG. 1.

As compared with the band of the supernatant obtained in the absence of particles (lane 7 in FIG. 1), the bands of supernatant of the mixture containing the St-GMA particles (lanes 1 to 3) were thin, namely, a considerable amount of protein had been adsorbed on the St-GMA particles. On the other hand, the bands of supernatant of the mixture containing the poly-GMA particles (lanes 4 to 6) were not different from the band in lane 7, indicating that no protein had been adsorbed on the poly-GMA particles. It is conjectured that styrene units were exposed at the surface of the St-GMA particles, resulting in hydrophobic binding of protein.

The above results indicate that the poly-GMA particles has no non-specific adsorbability for protein.

Furthermore, the poly-GMA particles have a specific gravity of as high as about 1.2 in spite of their submicron size, and therefore they are easy to precipitate and can easily be recovered.

EXAMPLE 2

Using a synthesizer, there were prepared 15-bp oligodeoxynucleosides:

5'-AAAACGGAAGTGACG-3'
3'-GCCTTCACTGCTTTT-5' which had a base sequence recognizable by a transcription-controlling protein E4TF1.

To the oligodeoxynucleosides were added γ-32p-ATP (which was not essentially necessary but added for measuring the degree of binding of DNA chains to a carrier in the Example 3 hereinafter given and for detecting the protein in Example 4), ATP and Kinase. The resulting mixture was incubated at 37° C. for 1 hour to phosphorylate the 5'-terminals, and the thus treated oligodeoxynucleosides were combined with each other by means of annealing and ligase treatment to prepare an approx. 200 bp DNA chain having projecting 5'-terminals.

EXAMPLE 3

The DNA chain prepared in Example 2 was attached to the poly-GMA particles prepared in Example 1, by a cyanogen bromide method. On the basis of previous investigation, it was attached under reaction conditions of a temperature of 2° C. and a pH of 11 to 12 under which the DNA chains could be attached to the poly-GMA particles with the highest efficiency. The proportion of cyanogen bromide to the particles was 3.0 g of cyanogen bromide to 240 mg of the particles. The poly-GMA particles having DNA chains immobilized thereon were recovered by centrifugation, after which the amount of DNA chains unbound to particles in the supernatant was determined from the amount of radiation of 32 p, and the amount of DNA chain immobilized was calculated. Consequently, it was found that 50 to 60% of the DNA chains used was immobilized on particles to give poly-GMA particles having DNA chain immobilized thereon in an amount of about 20 molecules per particle (0.6–1.0 μg/mg)

EXAMPLE 4

Figure 2:
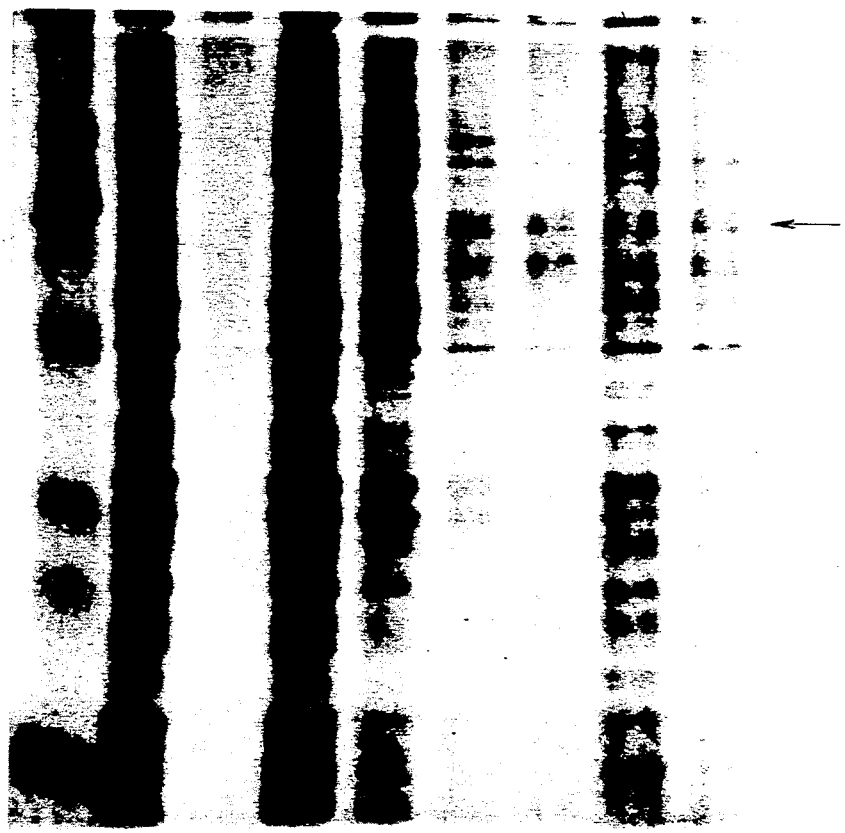
FIG. 2 shows the results of SDS-PAGE in each step of partial purification of E4TF1 protein.
Figure 3:
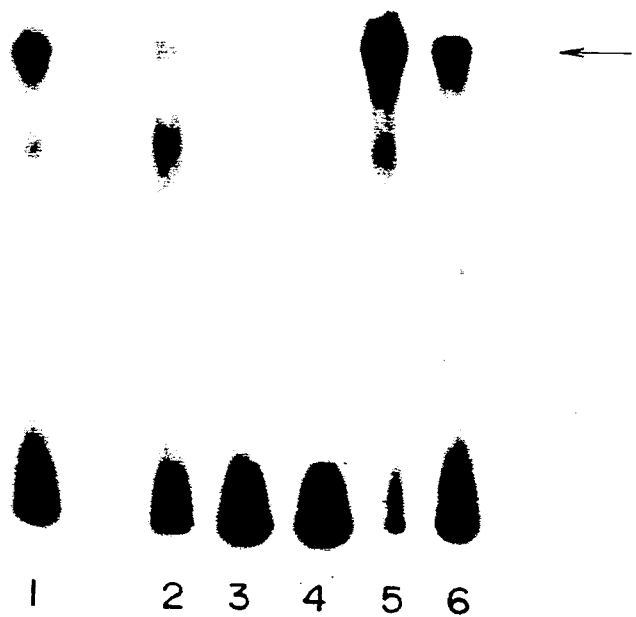
FIG. 3 shows the results of gel shift assay in each step of partial purification of E4TF1.

To the same protein solution as used in Example 1 was added 200 μg of the poly-GMA particles having DNA chain immobilized thereon, and after stirring by pipetting at 4° C. for 30 minuts, the poly-GMA particles having DNA chain immobilized thereon were separated from the supernatant by centrifugation. After sufficient washing with 0.1 M KCl Tris buffer (pH 7.9), the poly-GMA particles having DNA chain immobilized thereon was treated with 0.5 M KCl Tris buffer (pH 7.09) to elute the protein bound to the DNA chain. In FIG. 2 are shown the results of SDS-PAGE of the supernatant obtained in each step. In FIG. 3 are shown the results of gel shift assay comprising mixing the terminally labelled DNA prepared in Example 2 having an ability to bind to E4TF1, with a sample protein solution, electro-phoresing the resulting mixture in polyacrylamide gel, and thereby examining the protein-binding ability.

In FIG. 2, lane 1 is for size markers for protein, lane 2 is for the unpurified protein sample, lane 3 is for the protein solution (supernatant) after separation of the DNA-immobilized poly-GMA particles, lanes 4, 5 and 6 are for supernatants after the first, second and third washings, respectively, of the separated DNA-immobilized poly-GMA particles, and lanes 7 and 8 are for the partially purified protein E4TF1 obtained by the elution with 0.5 M KCl Tris buffer (pH 7.9) after the washings. E4TF1 appeared as a band at the position of the arrow. In this stage, contamination by other proteins was still considerable.

In FIG. 3, lane 1 is for the unpurified protein sample, lane 2 is for the protein solution (supernatant) after separation of the DNA-immobilized poly-GMA particles, lanes 3 and 4 are for supernatants after the first and second washings, respectively, of the separated DNA-immobilized poly-GMA particles, and lanes 5 and 6 are for partially purified E4TF1. From these results, it was found that E4TF1 retained its activity to bind to a specific base sequence(s), after the above purification.

The partially purified E4TF1 solution was diluted with Tris buffer to lower its salt concentration to 0.1 M, and then it was treated again by use of the DNA-immobilized poly-GMA particles to be purified. The purified E4TF1 thus obtained was subjected to SDS-PAGE. The results obtained are shown in FIG. 4.

Figure 4:
FIG. 4 shows the results of SDS-PAGE in each step of partial purification of E4TF1.
Figure 4:
Figure 4:

In FIG. 4, lane 1 is for is markers for protein, lane 2 is for the partially purified protein sample, lane 3 is for the protein solution (supernatant) after separation of the DNA-immobilized poly-GMA particles, and lane 4 is for purified E4TF1.

Thus, the transcription-controlling factor E4TF1 could be separated and purified very selectively.

What is claimed is:

1. A DNA-immobilized microsphere comprising DNA polynucleotide chains having base sequences to which a target protein specifically binds, and a carrier having a particle size of not more than 50 μm and not less than 0.01 μm which does not substantially absorb any protein, a surface of said carrier and said DNA polynucleotide chains being bound to each other by a chemical bond.

2. The DNA-immobilized-microsphere according to claim 1, wherein the particle size of the carrier is not more than 20 μm and not less than 0.2 μm.

3. The DNA-immobilized microsphere according to claim 1, wherein said protein is a transcription-controlling factor.

4. The DNA-immobilized microsphere according to claim 3, wherein the carrier has a surface which is not hydrophobic.

5. The DNA-immobilized microsphere according to claim 4, wherein the surface is made of at least one polymer obtained from at least one monomer selected from the group consisting of monoethylenic unsaturated amide monomers and ethylenic unsaturated nitrile compounds.

6. The DNA-immobilized microsphere according to claim 1, wherein the carrier has a surface which is not hydrophobic.

7. The DNA-immobilized microsphere according to claim 6, wherein the surface is made of at least one polymer obtained from at least one monomer selected from the group consisting of monoethylenic unsaturated amide monomers and ethylenic unsaturated nitrile compounds.

8. The DNA-immobilized microsphere according to claim 7 or 5, wherein the polymer is poly-GMA.

9. The DNA-immobilized microsphere according to claim 1, wherein the chemical bond between the surface of the carrier and the DNA polynucleotide chains is a covalent bond.

10. The DNA-immobilized microsphere according to claim 1, wherein the covalent bond is formed by a method selected from the group consisting of carbodiimide method, cyanogen bromide method, glutaraldehyde method, diazo method, and epoxy method.

* * * * *